US005484908A

United States Patent [19]
Froehler et al.

[11] Patent Number: 5,484,908
[45] Date of Patent: Jan. 16, 1996

[54] OLIGONUCLEOTIDES CONTAINING 5-PROPYNYL PYRIMIDINES

[75] Inventors: Brian Froehler, Belmont; Robert J. Jones, Daly City, both of Calif.

[73] Assignee: Gilead Sciences, Inc., Foster City, Calif.

[21] Appl. No.: 799,824

[22] Filed: Nov. 26, 1991

[51] Int. Cl.$^6$ ............................. C07H 21/00; C07H 21/04
[52] U.S. Cl. .......................... 536/24.31; 536/24.5
[58] Field of Search .................. 536/27, 23, 29, 536/28.52, 28.53, 24.3, 24.32, 24.5

[56] References Cited

FOREIGN PATENT DOCUMENTS

| | | |
|---|---|---|
| 375408 | 6/1990 | European Pat. Off. . |
| 0486477 | 5/1992 | European Pat. Off. . |
| WO89/12060 | 12/1989 | WIPO . |

OTHER PUBLICATIONS

Ötvös et al., "Substrate specificity of DNA polymerases. I. Enzyme-catalyzed incorporation of 5-(1-alkenyl)-2'-deoxyuridines into DNA" *Nucleic Acids Research* (1987) 15:(4):1763–1777.
Maher et al., *Science* (1989)245:725–730.
Moser and Dervan, *Science* (1987) 238:645–650.
Cooney et al., *Science* (1988) 241:456–459.
Griffin and Dervan, *Science* (1989) 245:967–971.
Beal and Dervan, *Science* (1990) 251:1360–1363.
Povsic and Dervan, *J. Am. Chem. Soc.* (1989) 111:3059–3061.
Vlassov et al., *Nucleic Acids Res.* (1986) 14:4065–4076.
Knorre et al., *Biochimie* (1985) 67:785–789.
Iverson and Dervan, *J. Am. Chem. Soc.* (1987) 109:1241–1243.
Meyer et al., *J. Am. Chem. Soc.* (1989) 111:8517–8519.
Lee et al., *Biochemistry* (1988) 27:3197–3203.
Horne and Dervan, *J. Am. Chem. Soc.* (1990) 112:2435–2437.
Webb and Matteucci, *J. Am. Chem. Soc.* (1986) 108:2764–2765.
Webb and Matteucci, *Nucleic Acids Res.* (1986) 14:7661–7674.
Matteucci and Webb, *Tetrahedon Letters* (1987) 28:2469–2472.
Praseuth et al., *Proc. Natl. Acad. Sci. (USA)* (1988) 85:1349–1353.
Vlassov et al., *Gene* (1988) 72: pp. 313–322.
Fedorova et al., *FEBS* (1988) 228:273–276.
Capobionco et al., *Nucleic Acids Res.* (1990) 18:2661–2669.
van de Sande et al., *Science* (1988) 241:551–557.
Uhlmann et al., *Chem. Reviews* (1990) 90:543–584.
van der Krol et al., *Biotechniques* (1988) 6:958–976.
Valko, K. et al., *Journal of Liquid Chromatography* (1989) 12(11):2103–2116 Correlation of Nucleotide Incorporation Rate and HPLC Retention Parameters of Substituted Nucleosides.
Valko, K. et al., *Journal of Chromatography* (1990) 506:35–44 Application of Chromatographic Retention Data in an Investigation of a Quantitative Structure–Nucleotide Incorporation Rate Relationship.
Otvos, L. et al., *Nucleic Acids Res* (1987) 1763–1777.
Balzarini et al., "Incorporation of 5-substituted pyrimidine nucleoside analogs into DNA of a thymidylate synthetase-deficient murine FM3A carcinoma cell line" *Chem. Abstracts* (1985) 103(3):(abstract No. 16283a).
Ötvös et al., "Substrate specificity of DNA polymerases. II. 5-(1-alkylnyl)-dUTPs as substrates of the Klenow DNA polymerase enzyme" *Chem. Abstracts* (1987) 107(23):(abstract No. 214012g).
Felgner et al., "Lipofection: a highly efficient, lipid-mediated DNA-transfection procedure" *Proc. Natl. Acad. Sci. USA* (1987) 84:7413–7417.
Chemical Abstracts 113(25):231937d. Rahim, EP Pat. Appl. 375164.

*Primary Examiner*—Douglas W. Robinson
*Assistant Examiner*—Gary L. Kunz
*Attorney, Agent, or Firm*—Daryl D. Muenchau

[57] ABSTRACT

Oligonucleotides with enhanced hybridization binding possessing 5-propynyluracil and/or 5-propynylcytosine in place of uracil and cytosine, respectively. These oligonucleotides are useful in traditional hybridization assays for detection of a specific DNA sequence.

18 Claims, No Drawings

5,484,908

OLIGONUCLEOTIDES CONTAINING 5-PROPYNYL PYRIMIDINES

TECHNICAL FIELD

The invention relates generally to novel nucleosides and oligonucleotide analogs, and to diagnosis by binding of the oligonucleotide analogs to single or double-stranded nucleic acid target sequences. More specifically, the invention concerns oligomers containing 5-substituted cytosine and uracil base residues and intermediates in their synthesis.

BACKGROUND ART

Sequence-specific binding of oligonucleotides both to single-stranded and to duplex DNA has been recognized. The appropriate sequence recognition for binding to single-stranded targets is well known: the A-T and G-C pairing characteristic of duplex formation has been established as the basis for DNA replication and transcription. More recently, it has been realized that oligonucleotides may also bind in a sequence-specific manner to duplex DNA in order to form triplexes.

Thus, duplex DNA can be specifically recognized by oligomers based on a recognizable nucleotide sequence. Two major recognition motifs have been recognized. In an earlier description of a "CT" motif, cytosine residues recognize G-C basepairs while thymine residues recognize A-T basepairs in the duplex. These recognition rules are outlined by Maher III, L. J., et al., *Science* (1989) 245:725–730; Moser, H. E., et al., *Science* (1987) 238:645– 650. More recently, an additional motif, called "GT" recognition, was described by Cooney, M., et al., *Science* (1988) 241:456–459; Hogan, M. E., et al., EP Publication 375408. In the G-T motif, A-T pairs are recognized by adenine or thymine residues and G-C pairs by guanine residues.

In both of these binding motifs, the recognition sequence must align with a sequence as played out on one of the chains of the duplex; thus, recognition, for example, of an A-T pair by a thymine depends on the location of repeated adenyl residues along one chain of the duplex and thymine series on the other. The recognition does not extend to alternating A-T-A-T sequences; only the adenyl residues on one chain or the other would be recognized. An exception to the foregoing is the recent report by Griffin, L. C., et al., *Science* (1989) 245:967–971, that limited numbers of guanine residues can be provided within pyrimidine-rich oligomers and specifically recognize thymine-adenine base pairs; this permits the inclusion of at least a limited number of pyrimidine residues in the homopurine target.

The two motifs exhibit opposite binding orientations with regard to homopurine target chains in the duplex. In the CT motif, the targeting oligonucleotide is oriented parallel to the target purine-rich sequence; in the GT motif, it is oriented antiparallel (Beal, P. A., et al., *Science* (1990) 251:1360–1363). Thus, recognition sequences in the CT motif are read with respect to target 5'→3' sequences so that in the 5'→3' direction, synthetic oligonucleotides contain the required sequence of C or T residues with respect to the guanine or adenyl residues in the target. In the GT motif, on the other hand, the targeted sequence is read 5'→3' in order to design the 3'→5' sequence of the targeting oligonucleotide.

One problem that has arisen with respect to binding in the CT system resides in the ionization state of the "C" residue at neutral or physiological pH. In order to form the appropriate hydrogen bond donor/acceptor pattern, the amino group at position 3 of the C must be protonated. This is consonant with the $pK_a$ when the pH is low (cytosine $pK_a$ is 4.25), but at neutral pH, most of the pyrimidines are unprotonated. This interferes with binding at physiological pH.

One proposed solution to this problem has been the use of 5-methylcytosine ($pK_a$ 4.35) instead of cytosine as the recognizing "C". This approach was based upon the observation (Lee, J. S. et al., *Nucleic Acids Res* (1984) 12:6603–6614) that polypyrimidine oligonucleotides composed of 5-methyldeoxycytidine can bind to poly G:poly C double-stranded DNA at neutral pH. The ability of both 5-bromouracil and 5-methylcytosine to bind duplex DNA at the same homopurine target sequence as their T/C analogs, but with greater affinities and over an extended pH range has also been reported by Povsic, T. J., et al., *J Am Chem Soc* (1989) 111:3059–3061. The improved binding of 5-methylcytosine compared to cytosine in CT mode binding is believed to result from (i) an increased $pK_a$, and (ii) interaction of the methyl group at position 5 with adjacent methyl groups in the oligomer. Another approach which was taken (Cooney, M.; Czernuszewicz, G.; Postel, E. H.; Flint, E. S. J.; and Hogan, M. E. *Science* (1988) 241:456–459) was the substitution of deoxyguanosine for deoxycytidine, and the substitution of deoxyadenosine for thymidine to yield an alternative binding motif.

Sequence-specific targeting of both single-stranded and duplex oligonucleotides has applications in diagnosis and analysis. Under some circumstances wherein such binding is to be effected, it is advantageous to stabilize the resulting duplex or triplex over long time periods.

Covalent crosslinking of the oligomer to the target provides one answer to this problem. Sequence-specific recognition of single-stranded DNA accompanied by covalent crosslinking has been reported by several groups. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785– 789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J Am Chem Soc* (1990) 112:2435–2437.

Use of $N^4$, $N^4$-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674. These papers also describe the synthesis of oligonucleotides containing the derivatized cytosine. Matteucci and Webb, in a later article in *Tetrahedron Letters* (1987) 28:2469–2472, describe the synthesis of oligomers containing $N^6$, $N^6$-ethanoadenine and the crosslinking properties of this residue in the context of an oligonucleotide binding to a single-stranded DNA.

In a recent paper, Praseuth, D., et al., *Proc Natl Acad Sci (U.S.A.)* (1988) 85:1349–1353, described sequence-specific binding of an octathymidylate conjugated to a photoactivatable crosslinking agent to both single-stranded and double-stranded DNA. A target 27-mer duplex containing a polyA tract showed binding of the octathymidylate in parallel along the polyA. Photoactivated crosslinking of the duplex with a p-azidophenacyl residue covalently linked to the terminus of the octathymidylate was achieved. While sequence-specific association occurred at the predicted region of the duplex, it appeared that the crosslinking reaction itself was not target specific. As photoactivation was required to form the covalent crosslink, there could be no question of accurate sequence-specific association of the octathymidylate to the target sequence in the 27-mer duplex. A requirement for photoactivation, however, seriously limits the therapeutic potential of the crosslinking agent. Administration to a live subject does not readily admit of this mechanism of action.

In addition, Vlassov, V. V. et al., *Gene* (1988) 313–322 and Fedorova, O. S. et al., *FEBS* (1988) 228:273– 276, describe targeting duplex DNA with a 5'-phospho-linked oligonucleotide.

In effecting binding to obtain a triplex, to provide for instances wherein purine residues are concentrated on one chain of the target and then on the opposite chain, oligonucleotides of inverted polarity may be provided. By "inverted polarity" is meant that the oligonucleotide contains tandem sequences which have opposite polarity, i.e., one having polarity 5'→3' followed by another with polarity 3'→5', or vice versa. This implies that these sequences are joined by linkages which can be thought of as effectively a 3'—3' internucleotide junction (however the linkage is accomplished), or effectively a 5'—5' internucleotide junction. Such oligomers have been suggested as by-products of reactions to obtain cyclic oligonucleotides by Capobionco, M. L., et al., *Nucleic Acids Res* (1990) 18:2661–2669. Compositions of "parallel-stranded DNA" designed to form hairpins secured with AT linkages using either a 3'—3' inversion or a 5'—5' inversion have been synthesized by van de Sande, J. H., et al., *Science* (1988) 241:551–557. In addition, triple helix formation using an oligomer which contains an effective 3'—3' linkage has been described by Horne, D. A., and Dervan, P. B., *J Am Chem Soc* (1900) 112:2435–2437.

Single-stranded nucleic acid, primarily RNA, is the target molecule for oligonucleotides that are used to inhibit gene expression by an "antisense" mechanism (Uhlmann, E., et al, *Chem Reviews* (1990) 90:543–584; van der Krol, A. R., et al, *Biotechniques* (1988) 6:958–976). Antisense oligonucleotides are postulated to exert an effect on target gene expression by hybridizing with a complementary RNA sequence. The hybrid RNA-oligonucleotide duplex appears to interfere with one or more aspects of RNA metabolism including processing, translation and metabolic turnover. Chemically modified oligonucleotides have been used to enhance their nuclease stability.

DISCLOSURE OF THE INVENTION

The invention provides oligomers containing a multiplicity of nucleotides wherein at least one nucleotide comprises a 5-substituted uracil or cytosine residue. Oligomers including these modified bases show enhanced binding capacities in the formation of duplexes or triplexes with single-stranded or duplex oligonucleotide targets, respectively. The substitution of 5-unsaturated alkenyl- or alkynyl-substituted uracil residues for thymine in oligomers which target DNA duplexes enhances the binding affinity. Substitution of thymine residues by the 5-substituted uracil residues of the invention or substitution of cytosine residues by the 5-substituted cytosine residues of the invention enhance the ability of the resulting oligomer to bind single-stranded DNA or RNA targets.

Accordingly, in one aspect, the invention is directed to an oligomer comprising a multiplicity of nucleotides wherein at least one said nucleotide comprises a base of the formula

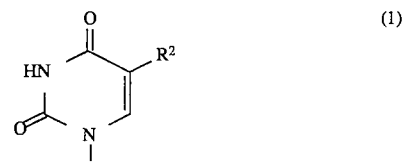 (1)

or

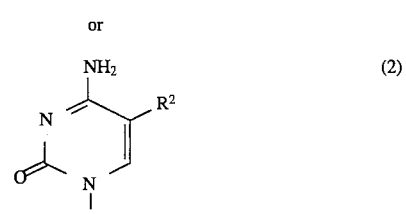 (2)

wherein $R^2$ is selected from the group consisting of propynyl (—C≡C—CH$_3$), propenyl (—CH=CH—CH$_3$), 3-buten-1-ynyl (—C≡C—CH=CH$_2$), 3-methyl-1-butynyl (—C≡C—CH(CH$_3$)$_2$), 3,3-dimethyl-1-butynyl (—C≡C—C(CH$_3$)$_3$), phenyl, m-pyridinyl, p-pyridinyl and o-pyridinyl.

In other aspects, the invention is directed to duplexes or triplexes obtained by binding the foregoing oligomers to duplex or single-stranded targets.

In other aspects, the invention is directed to intermediates in the synthesis of the oligomers of the invention, including nucleoside analogs of the formula:

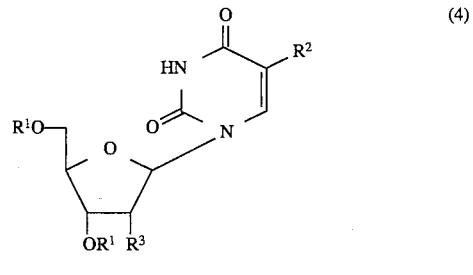 (4)

or

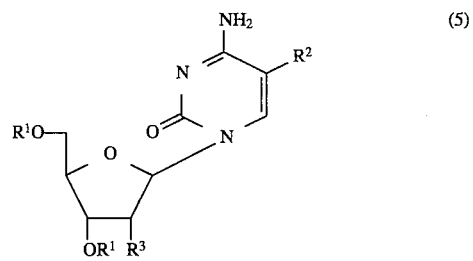 (5)

wherein
each $R^1$ is independently H or a blocking group;
$R^2$ is selected from the group consisting of propynyl, 3-buten-1-ynyl, 3-methyl-1-butynyl, 3,3-dimethyl-1-butynyl, propenyl, phenyl o-pyridinyl, m-pyridinyl and p-pyridinyl; and
$R^3$ is selected from the group consisting of H, OH, F, OCH$_3$, OC$_2$H$_5$, OC$_3$H$_7$, SCH$_3$, SC$_2$H$_5$, SC$_3$H$_7$, OC$_3$H$_5$, and $SC_3H_5$, with the proviso that if $R^3$ is H or OH, and both $R^1$ are H, $R^2$ cannot be propynyl.

Other useful intermediates in the synthesis of the oligomers of the invention include an o-xyloso nucleoside dimer having the general structural formula:

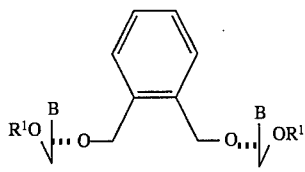
(6)

wherein each $R^1$ is H or a blocking group; and each B is independently a purine or pyrimidine base, provided that at least one B is

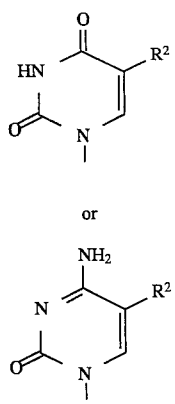
(1)

or (2)

wherein $R^2$ is selected from the group consisting of propynyl, 3-buten-1-ynyl, 3-methyl-1-butynyl, 3,3-dimethyl-1-butynyl, propenyl, phenyl, o-pyridinyl, m-pyridinyl and p-pyridinyl.

Also included are intermediates of the formula:

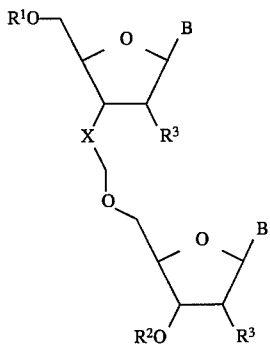
(8)

wherein

X is selected from the group consisting of O and S;

B is independently a purine or pyrimidine base, provided that at least one B is

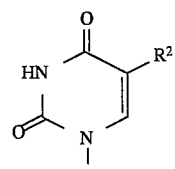
(1)

or

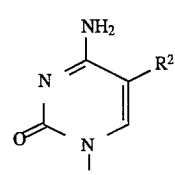
(2)

wherein each $R^1$ is independently selected from the group consisting of H and a blocking group;

each $R^2$ is independently selected from the group consisting of propynyl, 3-buten-1-ynyl, 3-methyl-1-butynyl, 3,3-dimethyl-1-butynyl, propenyl, phenyl o-pyridinyl, m-pryridinyl and p-pyridinyl; and each $R^3$ is independently selected from the group consisting of H, OH, F, $OCH_3$, $OC_2H_5$, $OC_3H_7$, $SCH_3$, $SC_2H_5$, $SC_3H_7$, $OC_3H_5$, or $SC_3H_5$.

A feature of the invention is that the oligomers of the invention can be comprised of a variety of different sequences and thereby used to target a variety of different single-stranded or double-stranded target sequences.

An advantage of the present invention is that the oligomers of the invention are capable of forming triplexes under physiological pH.

Another advantage of oligomers containing 5-$R^2$ substituted uracil or cytosine compared to oligomers containing thymine or cytosine is that the lipophilic group ($R^2$) may enhance cell permeation or uptake. The nucleosides containing these bases are more lipophilic than uridine, cytidine or thymidine based on retention times on HPLC.

MODES OF CARRYING OUT THE INVENTION

It has been found that the oligomers of the invention have enhanced binding properties with respect to complementary single-stranded and double-stranded nucleic acid sequences as compared to unmodified oligomers. Triple helix structures can be formed at physiological pH levels of 7.0 and higher, where unmodified control oligomers were less efficient. Improved duplex formation is also noted. The oligomers of the present invention are generally characterized as containing one or more pyrimidines modified at position 5. Preferred are modified C and U. The oligomers may also contain additional modifications in nucleotides that contain these 5-modified pyrimidines or in other nucleotides that comprise the oligomer. An exemplary list of such modifications include oligomers where (i) one or more nucleotide residues are modified at the 2' position, (ii) one or more crosslinking moieties have been incorporated, (iii) switchback linkers have been incorporated, (iv) substitute internucleotide linkages have been included and (v) other base analogs that facilitate triplex formation, such as 8-hydroxy-$N^6$-methyladenine, have been included. One or more of such modifications may advantageously be incorporated into a given oligomer depending on target nucleic acid sequences.

Substitution of 5-$R^2$ substituted U for T in oligomers results in enhanced ability to form triplexes and duplexes as compared with the oligomers containing thymine. These oligomers, in triplex formation, appear to recognize adenine residues in adenine-thymine base pairs and bind in the parallel CT triplex motif. Oligomers containing 5-$R^2$-C in place of C bind duplex DNA, but not as well as control oligomers containing 5-methylcytosine at corresponding positions. The reduced efficiency of triplex formation is believed to result primarily from the reduced $pK_a$ of the substituted base. In the 5 propynyl-substituted nucleoside corresponding to the nucleoside containing 5-methylcytosine, the $pK_a$ is only 3.30. The oligomers of the invention are thus capable of forming triplexes with various target sequences such as HER-2 and HIV sequences by coupling into the major groove of a target DNA duplex under physiological pH.

However, alteration of the heterocycle $pK_a$ as described above for the 5-$R^2$-C does not significantly affect binding to single-stranded target nucleic acid. In addition to binding efficiently to double-stranded target sequences, oligomers of the invention containing 5 -$R^2$ substituted U in place of T and/or 5 -$R^2$ substituted C in place of C were also found to bind single-stranded RNA efficiently. Oligomers containing either 5-$R^2$-C or 5-$R^2$-U formed duplex structures with complementary single-stranded RNA that had increased thermal stability ($T_m$) compared to the duplex formed by a control oligomer as described below. Compositions of the invention can be used for diagnostic purposes in order to detect the presence of neoplastic growth, viruses and a variety of disease conditions.

The invention has been summarized above. Before proceeding with a detailed description of the oligomers of the invention and their methods of synthesis and use, it is useful to provide a definition of some of the terms which will be used throughout this disclosure.

As used herein "oligonucleotide" or "oligomer" is generic to polydeoxyribonucleotides (containing 2'- deoxy-D-ribose or modified forms thereof), i.e., DNA, to polyribonucleotides (containing D-ribose or modified forms thereof), i.e., RNA, and to any other type of polynucleotide which is an N-glycoside or C-glycoside of a purine or pyrimidine base, or modified purine or pyrimidine base.

The oligomers of the invention may be formed using conventional phosphodiester-linked nucleotides and synthesized using standard solid phase (or solution phase) oligonucleotide synthesis techniques, which are now commercially available. However, the oligomers of the invention may also contain one or more "substitute" linkages as is generally understood in the art. These "substitute" linkages are defined herein as conventional alternative linkages such as phosphorothioate or phosphoramidate, are synthesized as described in the generally available literature. Substitute linkages that may be used in the oligomers disclosed herein also include nonphosphorous based internucleotide linkages such as the 3'-thioformacetal (—S—$CH_2$—O—), formacetal (—O—$CH_2$—O—) internucleotide linkages disclosed in U.S. Pat. 5,264,564. One or more substitute linkages may be utilized in the oligomers in order to further facilitate binding with complementary target nucleic acid sequences or to increase the stability of the oligomers toward nucleases.

The term "nucleoside" or "nucleotide" will similarly be generic to ribonucleosides or ribonucleotides, deoxyribonucleosides or deoxyribonucleotides, or to any other nucleoside which is an N-glycoside or C-glycoside of a purine or pyrimidine base, or modified purine or pyrimidine base. Thus, the stereochemistry of the sugar carbons may be other than that of D-ribose in one or more residues. Also included are analogs where the ribose or deoxyribose moiety is replaced by an alternate structure such as the 6-member morpholino ring described in U.S. Pat. No. 5,034,506 or where an acyclic structure serves as a scaffold that positions the base analogs described herein in a manner that permits efficient binding to target nucleic acid sequences. The enhanced efficiency of binding by oligomers containing the base analogs of the present invention is believed to be primarily a function of the base alone. Because of this, elements ordinarily found in oligomers, such as the furanose ring or the phosphodiester linkage may be replaced with any suitable functionally equivalent element.

"Nucleosides" or "nucleotides" also include those which contain modifications in the sugar moiety, for example, wherein one or more of the hydroxyl groups are replaced with halogen, aliphatic groups, or functionalized as ethers, amines, and the like.

Furthermore, as the α anomer binds to duplexes in a manner similar to that for the β anomers, one or more nucleotides may contain this linkage or a domain thereof. (Praseuth, D., et al., Proc Natl Acad Sci (U.S.A.) (1988) 85:1349–1353). Anomeric oligomers containing the 5-$R^2$ substituted pyrimidines described herein represent a class of modified oligomers included in the present invention.

"Nucleoside" and "nucleotide" include those moieties which contain not only the known purine and pyrimidine bases, but also heterocyclic bases which have been modified. Such modifications include alkylated purines or pyrimidines, acylated purines or pyrimidines, or other heterocycles. Such "analogous purines" and "analogous pyrimidines" are those generally known in the art, many of which are used as chemotherapeutic agents. An exemplary but not exhaustive list includes pseudoisocytosine, $N^4,N^4$-ethanocytosine, 8-hydroxy-$N^6$-methyladenine, 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyl uracil, dihydrouracil, inosine, $N^6$-isopentenyl-adenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyl uracil, 5-methoxy aminomethyl-2-thiouracil, beta-D-mannosylqueosine, 5'-methoxycarbonylmethyluracil, 5-methoxyuracil, 2-methylthio-$N^6$-isopentenyladenine, uracil-5-oxyacetic acid methyl ester, pseudouracil, 2-thiocytosine, 5-methyl-2-thiouracil, 2-thiouracil, 4-thiouracil, 5-methyluracil, N-uracil-5-oxyacetic acid methylester, uracil-5-oxyacetic acid, queosine, 2-thiocytosine, and 2,6-diaminopurine.

The oligomers of the present invention may be of any length, but lengths of greater than or equal to about 10 nucleotides, and preferably greater than about 15, are preferred. However, the longer oligonucleotides may also be made, particularly those of greater than 50 nucleotides or greater than 100 nucleotides.

Oligonucleotides may contain conventional internucleotide phosphodiester linkages or may contain modified forms such as phosphoramidate linkages. These alternative linking groups include, but are not limited to embodiments wherein a moiety of the formula P(O)S, ("thioate") P(S)S ("dithioate") P(O)N$R'_2$, P(O)R', alkyl (1–12C) and $R^6$ is alkyl (1–9C) is joined to adjacent nucleotides through —O— or —S—. Dithioate linkages are disclosed in U.S.

Pat. No. 5,194,599. Not all such linkages in the same oligomer need to be identical.

Also included are "derivatives" of oligonucleotides. "Derivatives" of the oligomers include those conventionally recognized in the art. For instance, the oligonucleotides may be covalently linked to various moieties such as intercalators, substances which interact specifically with the minor groove of the DNA double helix and other arbitrarily chosen conjugates, such as labels (radioactive, fluorescent, enzyme, etc.). These additional moieties may be derivatized through any convenient linkage. For example, intercalators, such as acridine can be linked through any available —OH or —SH, e.g., at the terminal 5' position of RNA or DNA, the 2' positions of RNA, or an OH, $NH_2$, COOH or SH engineered into the 5 position of pyrimidines, e.g., instead of the 5 methyl of thymine, a derivatized form which contains, for example, $—CH_2CH_2NH_2$, $—CH_2CH_2CH_2OH$ or $—CH_2CH_2CH_2SH$ in the 5 position. A wide variety of substituents can be attached, including those bound through conventional linkages. The indicated —OH moieties in the oligomers may be replaced by phosphonate groups, protected by standard protecting groups, or activated to prepare additional linkages to other nucleotides, or may be bound to the conjugated substituent. The 5' terminal OH may be phosphorylated; the 2'—OH or OH substituents at the 3' terminus may also be phosphorylated. The hydroxyls may also be derivatized to standard protecting groups.

Oligonucleotides or the segments thereof of are conventionally synthesized. Methods for such synthesis are found, for example, in Froehler, B., et al., *Nucleic Acids Res* (1986) 14:5399–5467; *Nucleic Acids Res* (1988) 16:4831–4839; *Nucleosides and Nucleotides* (1987) 6:287– 291; Froehler, B., *Tetrahedron Letters* (1986) 27:5575– 5578.

In addition to employing these very convenient and now most commonly used, solid phase synthesis techniques, oligonucleotides may also be synthesized using solution phase methods such as triester synthesis. These methods are workable, but in general, less efficient for oligonucleotides of any substantial length.

One group of oligomers of the present invention can be represented by the formula:

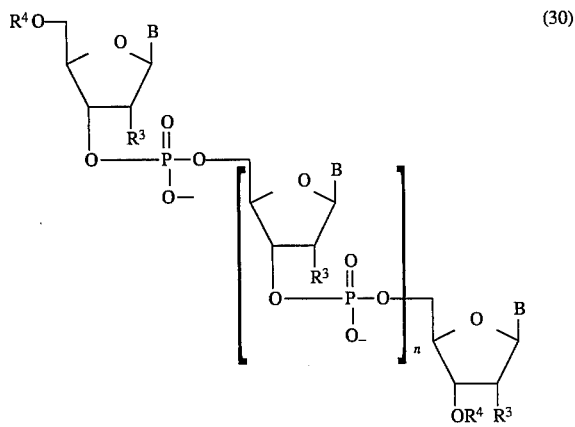

(30)

wherein each $R^3$ is independently selected from the group consisting of H, OH, F, $OCH_3$, $OC_2H_5$, $OC_3H_7$, $SCH_3$, $SC_2H_5$, $SC_3H_7$, $OC_3H_5$, and $SC_3H_5$;

each $R^4$ is independently selected from the group consisting of H, and a blocking group;

n is an integer from 4 to 30; and

B is a purine or pyrimidine base, provided that at least one B is

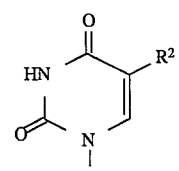

(1)

or

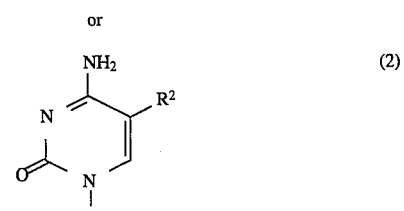

(2)

wherein $R^2$ is selected from the group consisting of propynyl, 3-buten-1-ynyl, 3-methyl-1-butynyl, 3,3-dimethyl-1-butynyl, propenyl, phenyl o-pyridinyl, m-pyridinyl and p-pyridinyl. This illustrative embodiment contains, as shown, standard phosphodiester linkages and has a sequence orientation in a single direction. However, other suitable oligomers of the invention may contain altered linkages other than phosphodiesters. Particularly useful forms of these linkages include formacetal, 5'-thioformacetal, and 3'-thioformacetal linkages. For synthesis of oligomers containing these formacetal-type linkages in lieu of the conventional phosphodiester linkage, the dimeric synthons of the formula:

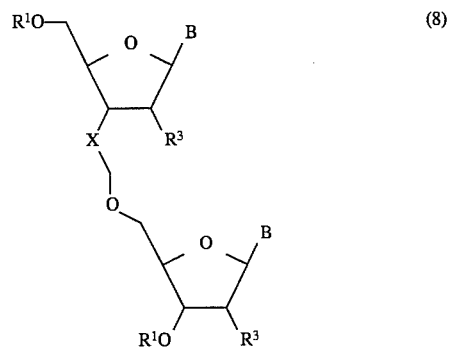

(8)

wherein the substituents B, X, $R^1$ and $R^3$ are as defined above are particularly useful. These synthons can be incorporated into an oligomer backbone using standard phosphodiester synthesis techniques. Further modifications of the resulting oligomers are described below.

Covalent Bonding Moiety

Included in some of the oligomers of the invention is a moiety which is capable of effecting at least one covalent bond between the oligomer and the duplex. Multiple covalent bonds can also be formed by providing a multiplicity of such moieties. The covalent bond is preferably to a base residue in the target strand, but can also be made with other portions of the target, including the saccharide or phosphodiester. The reaction nature of the moiety which effects crosslinking determines the nature of the target in the duplex. Preferred crosslinking moieties include acylating and alkylating agents, and, in particular, those positioned relative to the sequence specificity-conferring portion so as to permit reaction with the target location in the strand.

The crosslinking moiety can conveniently be placed as an analogous pyrimidine or purine residue in the sequence of the oligomer. The placement can be at the 5' and/or 3' ends, the internal portions of the sequence, or combinations of the above. Placement at the termini to permit enhanced flexibility is preferred. Analogous moieties can also be attached to peptide backbones.

In one preferred embodiment of the invention, a switchback oligonucleotide containing crosslinking moieties at either end can be used to bridge the strands of the duplex with at least two covalent bonds. In addition, nucleotide sequences of inverted polarity can be arranged in tandem with a multiplicity of crosslinking moieties to strengthen the complex.

Exemplary of alkylating moieties that are useful in the invention include $N^4,N^4$-ethanocytosine and $N^6,N^6$-ethanoadenine.

It is clear that the heterocycle need not be a purine or pyrimidine; indeed the pseudo-base to which the reactive function is attached need not be a heterocycle at all. Any means of attaching the reactive group is satisfactory so long as the positioning is correct.

Inverted Polarity

In their most general form, inverted polarity oligonucleotides, that may incorporate one or more nucleotide analogs described above, contain at least one segment along their length of the formula:

$$3'\text{———}\rightarrow 5'\text{——}C\text{——}5'\text{———}3' \quad (1)$$

or $$5'\text{———}\rightarrow 3'\text{——}C\text{——}3'\text{———}5' \quad (2)$$

where —C— symbolizes any method of coupling the nucleotide sequences of opposite polarity.

In these formulas, the symbol 3'5' indicates a stretch of oligomer in which the linkages are consistently formed between the 5' hydroxyl of the ribosyl residue of the nucleotide to the left with the 3' hydroxyl of the ribosyl residue of the nucleotide to the right, thus leaving the 5' hydroxyl of the rightmost nucleotide ribosyl residue free for additional conjugation. Analogously, 5'3' indicates a stretch of oligomer in the opposite orientation wherein the linkages are formed between the 3' hydroxyl of the ribosyl residue of the left nucleotide and the 5' hydroxyl of the ribosyl residue of the nucleotide on the right, thus leaving the 3' hydroxyl of the rightmost nucleotide ribosyl residue free for additional conjugation.

The linkage, symbolized by —C—, may be formed so as to link the 5' hydroxyls of the adjacent ribosyl residues in formula (1) or the 3' hydroxyls of the adjacent ribosyl residues in formula (2), or the "—C—" linkage may conjugate other portions of the adjacent nucleotides so as to link the inverted polarity strands. "—C—" may represent a linker moiety, or simply a covalent bond.

It should be noted that if the linkage between strands of inverted polarity involves a sugar residue, either the 3' or 2' position can be involved in the linkage, and either of these positions may be in either R or S configuration. The choice of configuration will in part determine the geometry of the oligomer in the vicinity of the linkage. Thus, for example, if adjacent 3' positions are used to effect a covalent linkage, less severe deformation of the oligonucleotide chain will generally occur if both 3' hydroxyls involved in the linkage are in the conventional R configuration. If they are both in the S configuration, this will result in a favorable "kink" in the chain.

In addition to the use of standard oligonucleotide synthesis techniques or other couplings to effect the 5'—5' or 3'—3' linkage between ribosyl moieties, alternative approaches to joining the two strands of inverted polarity may be employed. For example, the two appended bases of the opposing termini of the inverted polarity oligonucleotide sequences can be linked directly or through a linker, or the base of one can be linked to the sugar moiety of the other. Any suitable method of effecting the linkage may be employed. The characterizing aspect of the switchback oligonucleotides of the invention is that they comprise tandem regions of inverted polarity, so that a region of 3'→5' polarity is followed by one of 5'→3' polarity, or vice versa, or both.

Depending on the manner of coupling the segments with inverted polarity, this coupling may be effected by insertion of a dimeric nucleotide wherein the appropriate 3' positions of each member of the dimer or the 5' positions of each member of the dimer are activated for inclusion of the dimer in the growing chain, or the conventional synthesis can be continued but using for the condensing nucleotide a nucleotide which is protected/activated in the inverse manner to that which would be employed if the polarity of the chain were to remain the same. This additional nucleotide may also contain a linker moiety which may be included before or after condensation to extend the chain.

The synthesis of oligonucleotides having modified residues and/or inverted polarity may be accomplished utilizing standard solid phase synthesis methods.

In general, there are two commonly used solid phase-based approaches to the synthesis of oligonucleotides containing conventional 3'→5' or 5'→3' linkages, one involving intermediate phosphoramidites and the other involving intermediate phosphonate linkages. In the phosphoramidite based synthesis, a suitably protected nucleotide having a cyanoethylphosphoramidite at the position to be coupled is reacted with the free hydroxyl of a growing nucleotide chain derivatized to a solid support. The reaction yields a cyanoethylphosphite, which linkage must be oxidized to the cyanoethylphosphate at each intermediate step, since the reduced form is unstable to acid. The H-phosphonate-based synthesis is conducted by the reaction of a suitably protected nucleoside containing an H-phosphonate moiety at a position to be coupled with a solid phase-derivatized nucleotide chain having a free hydroxyl group, in the presence of a suitable activator to obtain an H-phosphonate diester linkage, which is stable to acid. Thus, the oxidation to the phosphate or thiophosphate can be conducted at any point during the synthesis of the oligonucleotide or after synthesis of the oligonucleotide is complete. The H-phosphonates can also be converted to phosphoramidate derivatives by reaction with a primary or secondary amine in the presence of carbon tetrachloride. To indicate the two approaches generically, the incoming nucleoside is regarded as having an "activated phosphite/phosphate" group.

Variations in the type of internucleotide linkage are achieved by, for example, using the methyl phosphonate precursors rather than the H-phosphonates per se, using thiol derivatives of the nucleoside moieties and generally by methods known in the art. Nonphosphorous based linkages may also be used, such as the formacetal 3'-thioformacetal, 3'-amino and 5'-ether type linkages described above.

Thus, to obtain an oligonucleotide segment which has a 3'→5' polarity, a nucleotide protected at the 5' position and containing an activated phosphite/phosphate group at the 3' position is reacted with the hydroxyl at the 5' position of a nucleoside coupled to a solid support through its 3'-hydroxyl. The resulting condensed oligomer is deprotected and the reaction repeated with an additional 5'-protected, 3'-phosphite/phosphate activated nucleotide. Conversely, to obtain an oligomeric segment of 5'→3' polarity, a nucleotide protected in the 3' position and containing an activated phosphite/phosphate in the 5' position is reacted with a nucleotide oligomer or nucleoside attached to a solid support through the 5' position, leaving the 3'-hydroxyl available to react. Similarly, after condensation of the incoming nucleotide, the 3' group is deprotected and reacted with an additional 3'-protected, 5'-activated nucleotide. The sequence is continued until the desired number of nucleotides have been added.

In addition to employing these very convenient and now most commonly used, solid phase synthesis techniques, oligonucleotides may also be synthesized using solution phase methods such as triester synthesis. These methods are workable, but in general, less efficient for oligonucleotides of any substantial length.

This oligonucleotide chain elongation will proceed in conformance with a predetermined sequence in a series of condensations, each one of which results in the addition of another nucleotide. Prior to the addition of a nucleoside having an activated phosphite/phosphate, the protecting group on the solid support-bound nucleotide is removed. Typically, for example, removal of the commonly-employed dimethoxytrityl (DMT) group is done by treatment with 2.5% v/v dichloroacetic acid/dichloromethane, although 1% w/v trichloroacetic acid/dichloromethane or $ZnBr_2$-saturated nitromethane, are also useful. Other deprotection procedures suitable for other protecting groups will be apparent to those of ordinary skill in the art. The deprotected nucleoside or oligonucleotide bound to solid support is then reacted with the suitably protected nucleotide containing an activated phosphite/phosphate. After each cycle the carrier bound nucleotide is preferably washed with anhydrous pyridine/acetonitrile (1:1, v/v), again deprotected, and the condensation reaction is completed in as many cycles as are required to form the desired number of congruent polarity internucleotide bonds which will be converted to phosphoramidates, phosphorodithioates, phosphorothioates or phosphodiesters as desired.

In one embodiment, to provide the switchback linker, the incoming activated, protected nucleoside is provided in the opposite polarity to the support-bound oligomers. Thus, for example, where the support-bound oligomer is 3'→5' the deprotected 5' hydroxyl is reacted with a 3'-protected, 5'-activated monomer, and the synthesis continued with monomers activated at the 5' position and protected at the 3' position.

In another embodiment, to provide the switchback linker, a dinucleoside synthon containing the linker element having one end which is activated for condensation (such as a hydrogen phosphonate) to the support-bound oligonucleotide and another end which is a protected hydroxyl group (or protected thio group) is condensed onto the support-bound oligonucleotide. The linked dinucleoside is condensed and deprotected using the same conditions as those used to condense and deprotect the protected nucleoside hydrogen phosphonate. Subsequent extension of the oligonucleotide chain then uses oligonucleotide residues which are activated and protected in the opposite manner from those used to synthesize the previous portion of the chain.

One approach to this synthesis, using a linker already derivatized to two nucleotide/nucleoside residues which will be included in each portion of the strand is illustrated in Reaction Scheme I. The 5'→3' nucleotide portion of the strand is coupled using the 3' DMT-5'-activated phosphate nucleosides, as conventionally, to solid support. The switchback linker is derivatized to two nucleotide residues through their 3' positions; the remaining 5' positions are derivatized by the protecting group DMT in one nucleotide residue and a phosphonate residue in the other. The derivatized linker is coupled to the solid supported strand under standard reagent conditions and then deprotected conventionally. Further standard nucleotide coupling results in extension of the chain in the 3'→5' orientation.

A particularly preferred dimer synthon used to mediate the switchback in an oligomer is the O-xyloso linker (compounds 4 and 5 in Reaction Scheme 1). The O-xyloso linker consists of two xylose-nucleosides (1) linked to each other by o-xylene at the 3' position of each xylose sugar. The switchback linker synthon was synthesized using α,α'-dibromoxylene and 5'-DMT nucleoside (1) to give the dimer (2) as shown in Reaction Scheme 1 below. The dimer was converted to the H-phosphonate (4) and was used in solid phase synthesis to generate oligomers. Linkers containing the bases (at position "B" in Reaction Scheme I) thymine, 5-methylcytosine, 8-hydroxy-$N^6$-methyladenine, pseudoisocytosine or cytosine are synthesized as homodimers. However, the switchback linker dimers may also be synthesized as mixed heterodimers that are separated chromatographically.

Reaction Scheme I

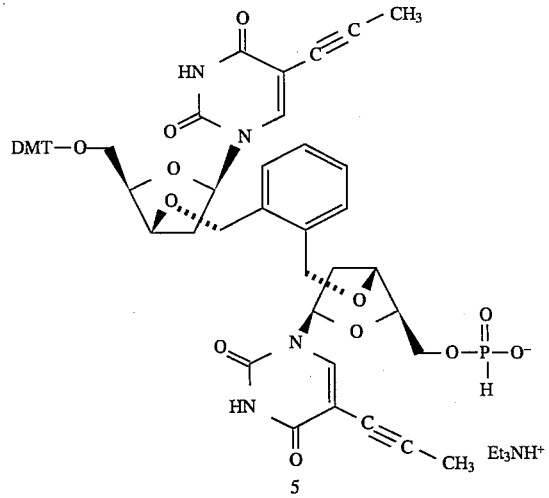

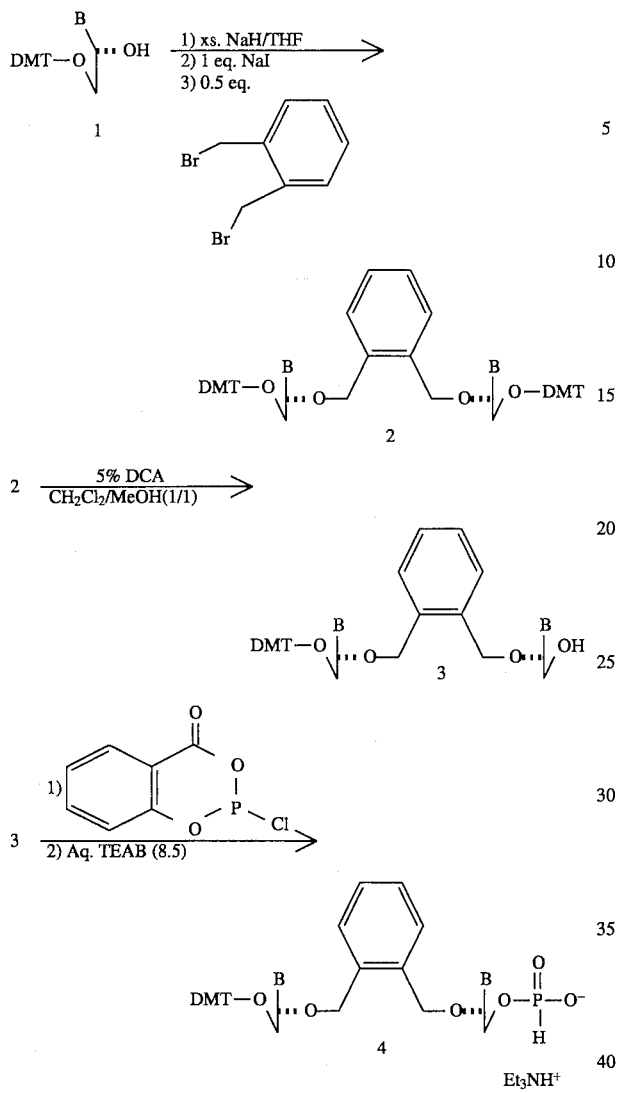

A particularly useful synthon in the preparation of oligomers containing inverted polarity is of the formula:

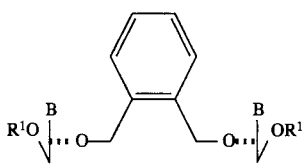

(6)

wherein each $R^1$ is H or a blocking group and each B is independently a purine or pyrimidine base, wherein one or both of these bases may optionally be the modified base residues of formula 1 and 2 of the invention.

2' Modified Oligomers

Included in some of the oligomers containing C-5 modified pyrimidines of the invention are modifications of the ribose or deoxyribose sugar. 2'—O—methyl-, 2'—O—ethyl- and 2'—O—allyloligo-ribonucleotides have been synthesized and shown to bind to single-stranded complementary nucleic acid sequences (Cotten, M., et al., *Nucleic Acids Res* (1990) 19:2629–2635; Blencowe, B. J., et al., *Cell* (1989) 59:531–539; Sproat, B. S., et al., *Nucleic Acids Res* (1989) 17:3373–3386; Inoue, H., et al., *Nucleic Acids Res* (1987) 15:6131– 6148; Morisawa, H., et al., European Patent Publication No. 0339842; Chavis, C., et al., *J Organic Chem* (1982) 47:202–206; Sproat, B. S., et al, *Nucleic Acids Res* (1991) 19:733–738). The 2'-modified oligomers were reported to be relatively nuclease stable compared to unmodified controls. Synthesis of 2' fluoro nucleosides and their incorporation into oligonucleotides has also been described (Codington, J. F., et al, *J Org Chem* (1964) 29:558–564; Fazakerley, G. V., et al, *FEBS Lett* (1985) 182:365–369). Synthesis of oligonucleotide analogs containing the modified bases described herein would be based on methods described.

Synthesis of 2'-thioalkyl nucleosides is accomplished as described in Reaction Scheme II. The protocol is useful for synthesis of 2'-thioalkyl pyrimidines which permit formation of an anhydro intermediate (2) that is subsequently converted to thioalkyl nucleoside (3). The protocol was used to synthesize 5' DMT blocked 5-methylcytidine 3' H-phosphonate. The starting material (1) was obtained from 5-methyluridine (Markiewicz, W. T., *J. Chem. Res (M)* (1979) 0181–0197. Alternate blocking groups at the 5' and 3' positions, such as tetrahydropyran may also be utilized to obtain an equivalent starting material. Scheme II may thus be used to synthesize 2'-thioalkyl derivatives of the nucleosides containing the modified bases of the present invention in addition to synthesis of other modified pyrimidine nucleosides such as 2'-thioalkylcytidine, 2'-thioalkylthymidine, 2'-thioalkyl-$N^4$-$N^4$-ethanocytidine or 2'-thioalkyluridine. Conversion of the nucleoside (3) to other 5' and 3' derivatized compounds such as MMT, β-cyanoethylphosphoramidite, or methylphosphoramidite-blocked nucleosides can easily be accomplished using appropriate reagents. (The group designated W may be lower alkane (methyl, ethyl, propyl, isopropyl, butyl or isobutyl) or lower alkene (allyl).)

Reaction Scheme II

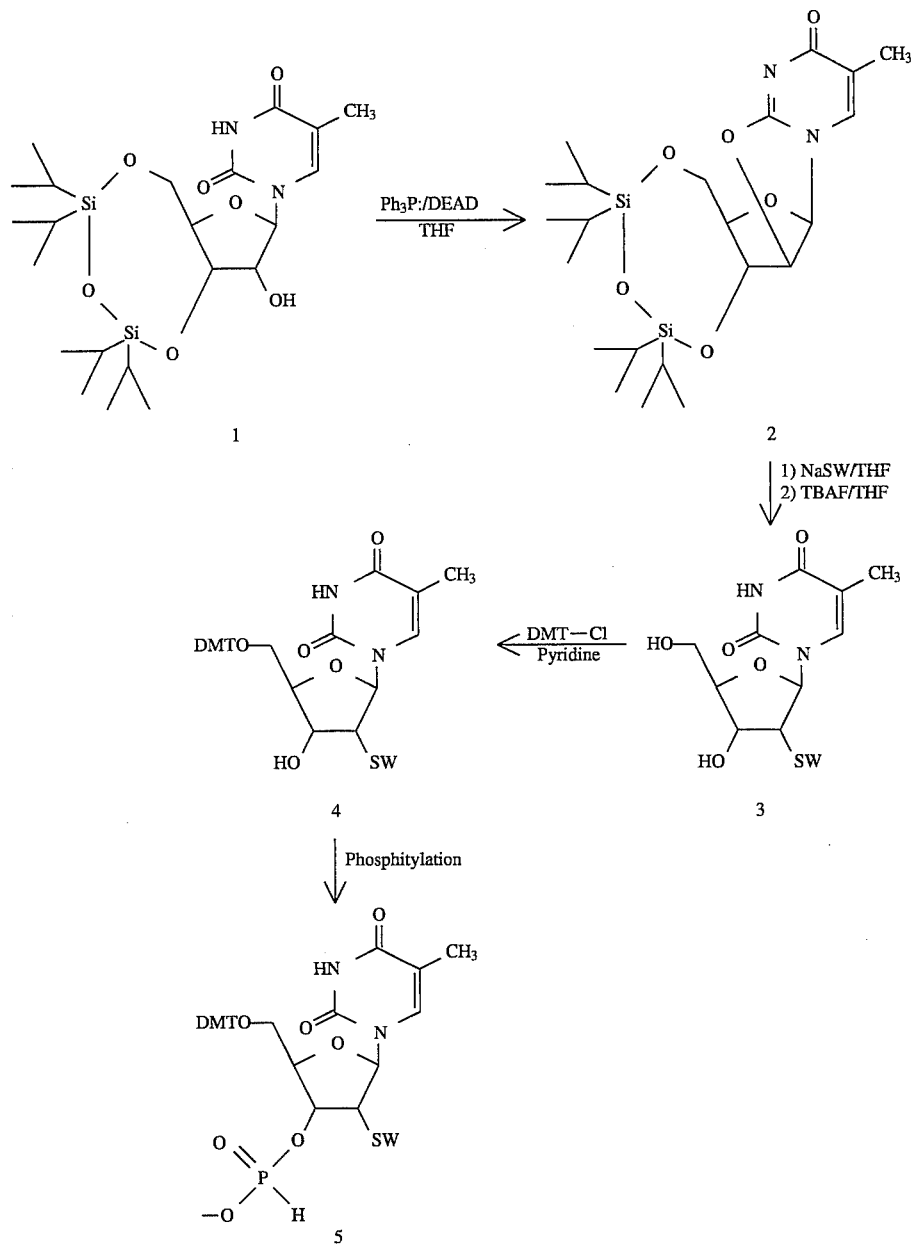

Dimer Synthons for Oligomers Containing Substitute Linkages

Oligomers containing substitute linkages that link adjacent nucleotide analog residues are preferably synthesized using suitably blocked dimer synthons as a starting material. For dimers wherein one or both base residues are 5-$R^2$-U or 5-$R^2$-C or related analogs, synthesis of a formacetal or 3'-thioformacetal-linked dimer is accomplished as described above. One or both starting monomers would consist of nucleosides containing 5-$R^2$-U or 5-$R^2$-C instead of conventional nucleosides. An exemplary dimer containing a formacetal linkage is of the formula:

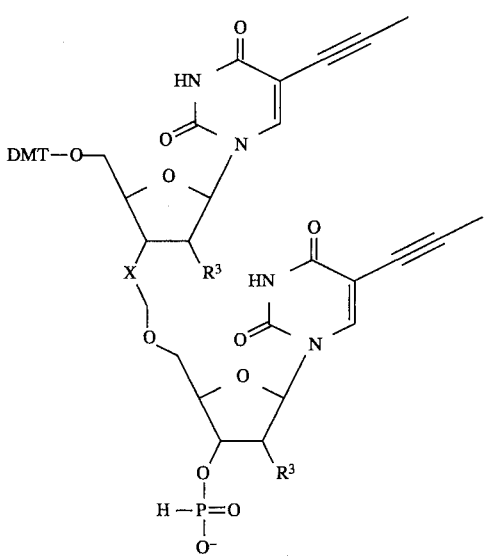

$R^3$ is as defined above and, in preferred embodiments, X is either O or S. Dimer synthons that are included in the scope of the present invention contain 5-$R^2$-U, 5-$R^2$-C or as one or both of the bases and may include (i) other substitute linkages such as the 3' amine linkage, (ii) other purines, pyrimidines or their analogs as described above or (iii) other 3' and 5' groups such as H, MMT, or an amidite as described above. Dimer synthons are incorporated into oligomers using any standard technique.

"Blocking Groups"

As used herein, "blocking group" refers to a substituent other than H that is conventionally coupled to oligomers or nucleosides, either as a protecting group, an activated group for synthesis, $PO_3^{-2}$, or other conventional conjugate partner such as a solid support, label, immunological carrier and the like. Suitable protecting groups are, for example, DMT or MMT; suitable activated groups are, for example, H-phosphonate, methyl phosphonate, methylphosphoramidite or β-cyanoethylphosphoramidite. In general, the nucleosides and oligomers of the invention may be derivatized to such "blocking groups" as indicated in the relevant formulas.

Utility and Administration

As the oligonucleotides of the invention are capable of significant single-stranded or double-stranded target nucleic acid binding activity to form duplexes, triplexes or other forms of stable association, these oligonucleotides are useful in diagnosis. Diagnostic applications for the oligomers described herein includes their use as probes for detection of specific sequences by any standard method.

In therapeutic applications, the oligomers are utilized in a manner appropriate for treatment of, for example, viral infections. For such therapy, the oligomers can be formulated for a variety of modes of administration, including systemic, topical or localized administration. Techniques and formulations generally may be found in *Remington's Pharmaceutical Sciences,* Mack Publishing Co., Easton, Pa., latest edition. The oligomer active ingredient is generally combined with a carrier such as a diluent or excipient which may include fillers, extenders, binders, wetting agents, disintegrants, surface-active agents, or lubricants, depending on the nature of the mode of administration and dosage forms. Typical dosage forms include tablets, powders, liquid preparations including suspensions, emulsions and solutions, granules, capsules and suppositories, as well as liquid preparations for injections, including liposome preparations.

For systemic administration, injection is preferred, including intramuscular, intravenous, intraperitoneal, and subcutaneous. For injection, the oligomers of the invention are formulated in liquid solutions, preferably in physiologically compatible buffers such as Hank's solution or Ringer's solution. In addition, the oligomers may be formulated in solid form and redissolved or suspended immediately prior to use. Lyophilized forms are also included. Dosages that may be used for systemic administration preferably range from about 0.01 mg/Kg to 50 mg/Kg administered once or twice per day. However, different dosing schedules may be utilized depending on (i) the potency of an individual oligomer at inhibiting the activity of its target gene, (ii) the severity or extent of a pathological disease state associated with a given target gene, or (iii) the pharmacokinetic behavior of a given oligomer.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents may be used to facilitate permeation. Transmucosal administration may be through use of nasal sprays, for example, or suppositories. For oral administration, the oligomers are formulated into conventional oral administration forms such as capsules, tablets, and tonics.

For topical administration, the oligomers of the invention are formulated into ointments, salves, gels, or creams, as is generally known in the art.

In addition to use in therapy, the oligomers of the invention may be used as diagnostic reagents to detect the presence or absence of the target gene sequences to which they specifically bind. Such diagnostic tests are conducted by hybridization through either double or triple helix formation which is then detected by conventional means. For example, the oligomers may be labeled using radioactive, fluorescent, or chromogenic labels and the presence of label bound to solid support detected. Alternatively, the presence of a double or triple helix may be detected by antibodies which specifically recognize these forms. Means for conducting assays using such oligomers as probes are generally known.

The use of oligomers containing the modified bases as diagnostic agents by triple helix formation is advantageous since triple helices form under mild conditions and the assays may thus be carried out without subjecting test specimens to harsh conditions. Diagnostic assays based on detection of RNA for identification of bacteria, fungi or protozoa sequences often require isolation of RNA from samples or organisms grown in the laboratory, which is laborious and time consuming; as RNA is extremely sensitive to ubiquitous nucleases.

The oligomer probes may also incorporate additional modifications such as altered internucleotide linkages that render the oligomer especially nuclease stable, and would thus be useful for assays conducted in the presence of cell or tissue extracts which normally contain nuclease activity. Oligonucleotides containing terminal modifications often retain their capacity to bind to complementary sequences without loss of specificity (Uhlmann et al., *Chemical Reviews* (1990) 90:543–584). As set forth above, the invention probes may also contain linkers that permit specific binding to alternate DNA strands by incorporating a linker that permits such binding (Horne et al., *J Am Chem Soc* (1990) 112:2435–2437).

Incorporation of base analogs of the present invention into probes that also contain covalent crosslinking agents has the potential to increase sensitivity and reduce background in diagnostic or detection assays. In addition, the use of crosslinking agents will permit novel assay modifications such as (1) the use of the crosslink to increase probe discrimination, (2) incorporation of a denaturing wash step to reduce background and (3) carrying out hybridization and crosslinking at or near the melting temperature of the hybrid to reduce secondary structure in the target and to increase probe specificity. Modifications of hybridization conditions have been previously described (Gamper et al., *Nucleic Acids Res* (1986) 14:9943).

The following examples are put forth so as to provide those of ordinary skill in the art with a complete disclosure and description of how to make the compounds and compositions of the invention and are not intended to limit the scope of what the inventors regard as their invention. Efforts have been made to insure accuracy with respect to numbers used (e.g., amounts, temperatures, etc.), but some experimental errors and deviations should be taken into account. Unless indicated otherwise, parts are parts by weight, temperature is in degrees Centigrade, and pressure is at or near atmospheric.

EXAMPLE 1

Synthesis of 5-Propynyl 2'-deoxyuridine H-Phosphonate Monomer and Oligomers Containing the Analog In a 50 mL round bottom flask is placed:

a) 708 mg (2 mmole) 5-iodo dU b) 10 mL anhydrous DMF c) 76 mg (0.4 mmole) CuI d) 555 µL (4 mmole) Et$_3$N e) 231 mg (0.2 mmole) (Ph$_3$P)$_4$Pd f) saturate with propyne gas with stirring at room temperature (approx. 10 min.).

After 2 hours, more propyne gas is bubbled in and the reaction mixture is stirred overnight at room temperature. The following morning more propyne is bubbled in and stirred for an additional 2 hrs. To the reaction mixture is added Dowex ion-exchange resin (HCO$_3$-form), 10 mL of MeOH and 10 mL of CH$_2$Cl$_2$ and stirring continued for 1 hr. The resin is filtered off, washed with MeOH and the supernatant evaporated. Silica gel chromatography yielded 517 mg (1.94 mmole, 97% yield) of product. See: Hobbs, *J Org Chem* (1989) 54:3420–3422.

The purified material was protected with a 5' DMT and phosphytylated as described (Marugg, J. E., et al, *Tetrahedron Letters* (1986) 27:2661–2664) and used in solid phase synthesis as described (Froehler, B. C., et al, U.S. Pat. No. 4,959,463; Froehler, B. C., et al, *Tetrahedron Letters* (1986) 27:5575–5578).

EXAMPLE 2

Formation of Triple Helix Structures Using Oligomers Containing 5-Propynyl Uracil Residues that Bind to Duplex DNA Three oligomers were synthesized as follows:

ODN-1 (SEQ ID NO: 1) 5'TCTCTCTCTCTTTTT 3'

ODN-2 (SEQ ID NO:2) TCTCTCTCTCUUUUU 3'

ODN-3 (SEQ ID NO:3) TCTCTCUCUCUTUTU 3'

Base residues designated U correspond to 5-propynyl uracil while T corresponded to thymine and C corresponded to 5-methylcytosine. The oligomer was hybridized with duplex DNA containing the target sequence (SEQ ID NO:1) 5'AGAGAGAGAGAAAAA 3'. Hybridization was carried out in 140 mM KCl, 5 mM MgCl$_2$, 5 mM Na$_2$HPO$_4$, pH 6.6. Thermal stability, $T_m$, of the resulting triple helix formed between each oligomer and the target sequence was determined. The following $T_m$ values were obtained, ODN-1(control oligomer) was 42.1° C., ODN-2 was 48.1° C. and ODN-3 was 55° C. The increased $T_m$ values of ODN-2 and ODN-3 were not expected and demonstrated that the triple helix formed was more stable than the corresponding control triple helix structure.

EXAMPLE 3

Binding of Oligomers Containing 5-Propynyl Uracil or 5-Propynyl Cytosine to Single-Stranded RNA Oligomers were synthesized as follows:

ODN-1 (SEQ ID NO:1) 5'TCTCTCTCTCTTTTT 3'

ODN-3 (SEQ ID NO:3) 5'TCTCTCUCUCUTUTU 3'

ODN-4 (SEQ ID NO:5) 5'TC*TC*TC*TC,TC,TTTTT 3'

Base residues designated C* correspond to 5-propynylcytosine while T, C and U are as defined in Example 2. The oligomers were hybridized with a single-stranded target RNA sequence, (SEQ ID NO:6) 5'AAAAA-GAGAGAGAGA 3', in 140 mM KCl, 5 mM MgCl$_2$, 5 mM Na$_2$HPO$_4$, pH 7.2. The following $T_m$ values for the duplexes were obtained; ODN- 1 (control) was 65.5° C., ODN-3 was 74.0° C. and ODN-4 was 73.0° C. Duplexes formed with ODN-3 and ODN-4 were more stable than the control oligomer.

EXAMPLE 4

Formation of Triple Helix Structures at Elevated pH

Triple helix formation at elevated pH was demonstrated using ODN-1 as a control and ODN-4, 5'UCUCUCUCU-CUUUUU 3'. Oligomers were hybridized with duplex target DNA as described in Example 2 except that the buffer was at pH 7.4. $T_m$ values of the triple helix were then determined. ODN-1 had a $T_m$ of 27.1 while ODN- 4 had a $T_m$ of 51.5. Thus, oligomers containing 5-propynyl uracil were capable of triplex formation at high pH levels, while the control oligomer formed triplex structure only at temperatures that are below physiological.

EXAMPLE 5

Synthesis of 3-Methyl-1-Butynyldeoxyuridine (bdU) H-Phosphonate, Oligomers Containing the Analog and Formation of Triple Helix Structures Using the Oligomers bdU was synthesized from 5-iododeoxyuridine essentially as described for pdU in Example 1, except that 5 equivalents of 3-methyl-1-butyne liquid was used in place of propyne. Silica gel purified material was then converted to the 5'DMT, 3' H-phosphonate monomer and used in solid phase synthesis to generate oligomers as follows (ODN-1 was used as a control containing thymine and 5-methylcytosine as described in Example 2):

ODN-1 (SEQ ID NO:1) 5'TCTCTCTCTCTTTTT 3'
ODN-5 (SEQ ID NO:8) 5'CTCTCU'CU'CU'TU'TU' 3'
ODN-6 (SEQ ID NO:9) 5'TCTCTCTCTCU'U'U'U'U' 3

Base residues designated U' correspond to bdU. The oligomers were hybridized with duplex DNA containing the target sequence (SEQ ID NO:4), 5'AGAGAGAGAGAAAAA 3'. Hybridization was carried out in the buffer described in Example 2 at pH 6.2. ODN-1 had a $T_m$ of 51.0° C. while the $T_m$ of ODN-5 was 55.2° C. and that of ODN-6 was 55.0° C.

Synthesis of 5-phenyldeoxyuridine was accomplished as previously described using phenyltrimethylstannane (Crisp, G., et al., *Tetrahedron Letters* (1990) 31:1347–1350). A similar protocol using pyridinyltrimethylstannane as a starting material which is obtained from bromo-pyridine would be used to synthesize 5-pyridinyluridine.

The instant invention is shown and described herein in what is considered to be the most practical and preferred embodiments. It is recognized, however, that departures may be made therefrom which are within the scope of the invention, and that modifications will occur to those skilled in the art upon reading this disclosure.

---

We claim:

1. A nucleoside analog having the general structural formula:

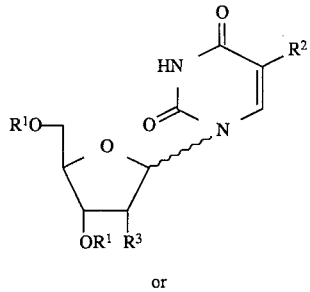
(4)

or

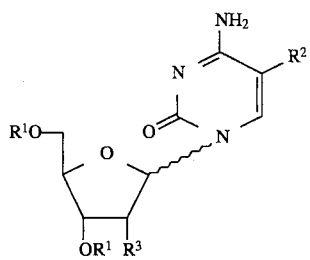
(5)

wherein in each of formula 4 and formula 5 one $R^1$ is a protecting group and the other is an activated group for oligonucleotide synthesis or is a solid support;

$R^2$ is selected from the group consisting of propynyl, 3-buten-1-ynyl, 3-methyl-1-butynyl, 3,3-dimethyl-1-butynyl, propenyl, phenyl, o-pyridinyl, m-pyridinyl and p-pyridinyl; and $R^3$ is selected from the group consisting of H, OH, F, $OCH_3$, $OC_2H_5$, $OC_3H_7$, $SCH_3$, $SC_2H_5$, $SC_3H_7$, $OC_3H_5$, and $SC_3H_5$.

2. The nucleoside analog of claim 1, wherein the protecting group is DMT (dimethoxytrityl) or MMT (monomethoxytrityl).

3. The nucleoside analog of claim 1 wherein $R^3$ is H or OH.

4. The nucleoside analog of claim 1 wherein $R^2$ is propynyl.

5. The nucleoside analog of claim 1 wherein the nucleoside is an α anomer.

6. An o-xyloso nucleoside dimer having the general structural formula:

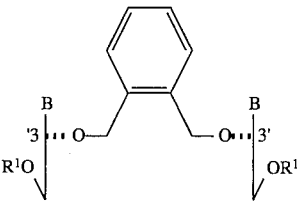
(6)

wherein each $R^1$ is H or a blocking group; and each B is independently a purine or pyrimidine base, provided that at least one B is

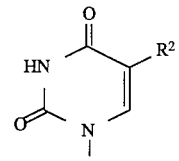
(1)

or

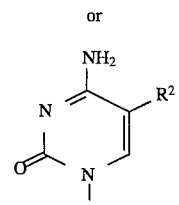
(2)

wherein $R^2$ is selected from the group consisting of propynyl, 3-buten-1-ynyl, 3-methyl-1-butynyl, 3,3-dimethyl-1-butynyl, propenyl, phenyl, o-pyridinyl, m-pyridinyl and p-pyridinyl.

7. The nucleoside dimer of claim 6 wherein $R^2$ is propynyl.

8. The nucleoside dimer of claim 7 wherein the blocking group is selected from the group consisting of $PO_3^{-2}$, DMT MMT H-phosphonate, methyl phosphonate, methylphosphoramidite, or β-cyanoethylphosphoramidite.

9. A nucleoside analog dimer having the general structural formula 8:

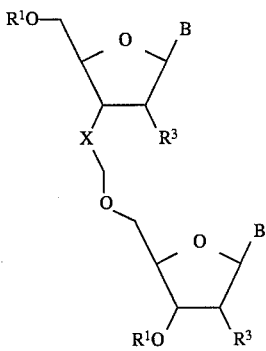

(8)

wherein

X is selected from the group consisting of O and S;

B is independently a purine or pyrimidine base, provided that at least one B is

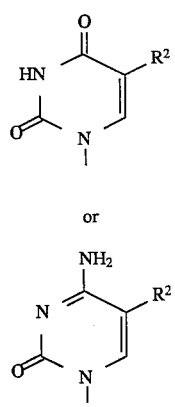

(1)

or (2)

wherein each $R^1$ is independently selected from the group consisting of H and a blocking group;

each $R^2$ is independently selected from the group consisting of propynyl, 3-buten-1-ynyl, 3-methyl-1-butynyl, 3,3-dimethyl-1-butynyl, propenyl, phenyl o-pyridinyl, m-pryridinyl and p-pyridinyl; and each $R^3$ is independently selected from the group consisting of H, OH, F, $OCH_3$, $OC_2H_5$, $OC_3H_7$, $SCH_3$, $SC_2H_5$, $SC_3H_7$, $OC_3H_5$, or $SC_3H_5$.

10. The dimer of claim 9 wherein $R^1$ is H, $PO_3^{-2}$, DMT, MMT, H-phosphonate, methylphosphoramidite or β-cyanoethylphosphoramidite.

11. The dimer of claim 9 wherein at least one B is 5-propynyluracil, 3-methyl-1-butynyluracil or 5-propynylcytosine.

12. The dimer of claim 9 wherein at least one $R^2$ is propynyl, $R^3$ is $OC_3H_5$ and X is S.

13. The nucleoside analog of claim 1 wherein the activated group is H-phosphonate, methyl phosphonate, methylphosphoramidite or β-cyanoethylphosphoramidite.

14. The nucleoside analog of claim 1 wherein $R^1$ at the 5' position is DMT (dimethoxytrityl) or MMT (monomethoxytrityl); $R^1$ at the 3' position is H-phosphonate, β-cyanoethylphosphoramidite or methylphosphoramidite; $R^2$ is propynyl or 3-methyl-1-butynyl; and $R^3$ is H.

15. The dimer of claim 6 wherein one of $R^1$ is a protecting group and the other of $R^1$ is an activated group for oligonucleotide synthesis or is a solid support.

16. The dimer of claim 15 wherein the activated group is H-phosphonate, methyl phosphonate, methylphosphoramidite or β-cyanoethylphosphoramidite.

17. The dimer of claim 9 wherein one of $R^1$ is a protecting group and the other of $R^1$ is an activated group for oligonucleotide synthesis or is a solid support.

18. The dimer of claim 17 wherein the activated group is H-phosphonate, methyl phosphonate, methylphosphoramidite or β-cyanoethylphosphoramidite.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1
        ( D ) OTHER INFORMATION: /note="T corresponds to thymine
            and C corresponds to 5-methylcytosine."

( x i ) SEQUENCE DESCRIPTION: SEQ ID NO:1:

TCTCTCTCTC TTTTT                                                                 1 5

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1
        ( D ) OTHER INFORMATION: /note="U corresponds to
            5-propynyl uracil, T corresponds to thymine, and
            C corresponds to 5-methylcytosine."

( x i ) SEQUENCE DESCRIPTION: SEQ ID NO:2:

TCTCTCTCTC UUUUU                                                                1 5

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 1
        ( D ) OTHER INFORMATION: /note="U corresponds to
            5-propynyl uracil, T corresponds to thymine and C
            corresponds to 5-methylcytosine."

( x i ) SEQUENCE DESCRIPTION: SEQ ID NO:3:

TCTCTCUCUC UTUTU                                                                                      15

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:4:

AGAGAGAGAG AAAAA                                                                                      15

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 2
        (D) OTHER INFORMATION: /note="C corresponds to
            5- propynylcytosine."

(xi) SEQUENCE DESCRIPTION: SEQ ID NO:5:

TCTCTCTCTC TTTTT                                                                                      15

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:6:

AAAAAGAGAG AGAGA                                                                                      15

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:7:

UCUCUCUCUC UUUUU                                                                                      15

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 7
        (D) OTHER INFORMATION: /note="U corresponds to bdU."

(xi) SEQUENCE DESCRIPTION: SEQ ID NO:8:

TCTCTCUCUC UTUTU                                                                                      15

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 11
        (D) OTHER INFORMATION: /note="U corresponds to bdU."

(xi) SEQUENCE DESCRIPTION: SEQ ID NO:9:

TCTCTCTCTC UUUUU        15